US012605110B2

(12) United States Patent
Shouldice et al.

(10) Patent No.: US 12,605,110 B2
(45) Date of Patent: Apr. 21, 2026

(54) TONGUE FAT SCREENING ASSAY

(71) Applicant: RESMED SENSOR TECHNOLOGIES LIMITED, Dublin (IE)

(72) Inventors: Redmond Shouldice, Dublin (IE); Jose Ricardo Dos Santos, San Diego, CA (US); Jeffrey Peter Armitstead, Bella Vista (AU)

(73) Assignee: RESMED SENSOR TECHNOLOGIES LIMITED, Dublin (IE)

( * ) Notice: Subject to any disclaimer, the term of this patent is extended or adjusted under 35 U.S.C. 154(b) by 0 days.

(21) Appl. No.: 18/269,501

(22) PCT Filed: Jan. 7, 2022

(86) PCT No.: PCT/US2022/011581
§ 371 (c)(1),
(2) Date: Jun. 23, 2023

(87) PCT Pub. No.: WO2022/150568
PCT Pub. Date: Jul. 14, 2022

(65) Prior Publication Data
US 2023/0389863 A1　　Dec. 7, 2023

Related U.S. Application Data

(60) Provisional application No. 63/135,881, filed on Jan. 11, 2021.

(51) Int. Cl.
*A61B 5/00*　　(2006.01)
*A61B 5/01*　　(2006.01)
(Continued)

(52) U.S. Cl.
CPC ........... *A61B 5/4818* (2013.01); *A61B 5/015* (2013.01); *A61B 5/0507* (2013.01);
(Continued)

(58) Field of Classification Search
None
See application file for complete search history.

(56) References Cited

U.S. PATENT DOCUMENTS 9,269,731 B2　2/2016　Sengupta et al.
11,937,938 B1 *　3/2024　Bianchi ................ A61B 5/7221
(Continued)

FOREIGN PATENT DOCUMENTS

EP　　　3061493 A1　8/2016
JP　　　2015093133 A　5/2015
(Continued)

OTHER PUBLICATIONS

Evaluation of Fat Tissue Deposition Within the Tongue via Near-Infrared Interactance, Journal of Dental Sleep Medicine, vol. 6, No. 4 (Year: 2019).*
(Continued)

*Primary Examiner* — Jonathan Cwern
(74) *Attorney, Agent, or Firm* — NIXON PEABODY LLP; Bradley M. Taub; Mark J. Fitzgerald

(57) ABSTRACT

The disclosure provides methods for diagnosis or prediction of the likelihood of a subject experiencing obstructive sleep apnea, determined at least in part by measuring the degree of tongue fat in a subject using, e.g., thermal imaging, THz imaging or other multispectral imaging.

19 Claims, 3 Drawing Sheets

(51) Int. Cl.

| | |
|---|---|
| *A61B 5/0507* | (2021.01) |
| *G06T 7/00* | (2017.01) |
| *G06V 10/143* | (2022.01) |
| *G06V 10/764* | (2022.01) |

(52) U.S. Cl.
CPC .......... *A61B 5/4552* (2013.01); *A61B 5/7275* (2013.01); *G06T 7/0012* (2013.01); *G06T 7/97* (2017.01); *G06V 10/143* (2022.01); *G06V 10/764* (2022.01); *G06T 2200/24* (2013.01); *G06T 2207/10048* (2013.01); *G06T 2207/30004* (2013.01); *G06V 2201/03* (2022.01)

(56) References Cited

U.S. PATENT DOCUMENTS

| | | | | |
|---|---|---|---|---|
| 2007/0239056 | A1* | 10/2007 | Moore | A61B 5/113 600/407 |
| 2015/0051449 | A1* | 2/2015 | Qiu | A61B 5/0836 600/407 |
| 2019/0083026 | A1* | 3/2019 | Radmand | A61B 6/512 |
| 2019/0200918 | A1 | 7/2019 | Chai et al. | |

FOREIGN PATENT DOCUMENTS

| | | | |
|---|---|---|---|
| WO | 2013/098435 | A1 | 7/2013 |
| WO | 2020/079437 | A1 | 4/2020 |

OTHER PUBLICATIONS

International Search Report in International Patent Application No. PCT/US2022/011581 mailed Jun. 3, 2022 (4 pp.).

Written Opinion in International Patent Application No. PCT/US2022/011581 mailed Jun. 3, 2022 (7 pp.).

Rosenthal R.D., "The Use of Near-IR Light to Measure Body Fat", presented at Scandinavian Weight Reduction Technical Conference, Oslo Norway, Jan. 1991, 26 pp.

Mustafa et al., "Near infrared spectroscopy for body fat sensing in neonates: quantitative analysis by GAMOS simulations", Biomed. Eng., Online 16:14 (2017), 17 pp.

Salamunes A.C.C. et al., "Application of thermal imaging for the assessment of body composition in humans", in Thermal Imaging, pp. 61-79, Edition 1, Chapter 3, 2017 Nova Science Publishers, Inc.

Mittleman D.M. et al., "T-Ray Imaging", IEEE Journal of Selected Topics in Quantum Electronics, vol. 2, No. 3, Sep. 1996, pp. 679-692.

Humphreys K. et al., "Medical applications of Terahertz Imaging: a Review of Current Technology and Potential Applications in Biomedical Engineering", Proceedings of the 26th Annual International Conference of the IEEE EMBS, : Sep. 2004, pp. 1302-1305, San Francisco CA.

Wilmink G.J. et al., "Development of a compact terahertz time-domain spectrometer for the measurement of the optical properties of biological tissues", Journal of Biomedical Optics 16(4): 047006, Apr. 2011, 12 pp.

* cited by examiner muscle adipose
tissue muscle adipose
tissue

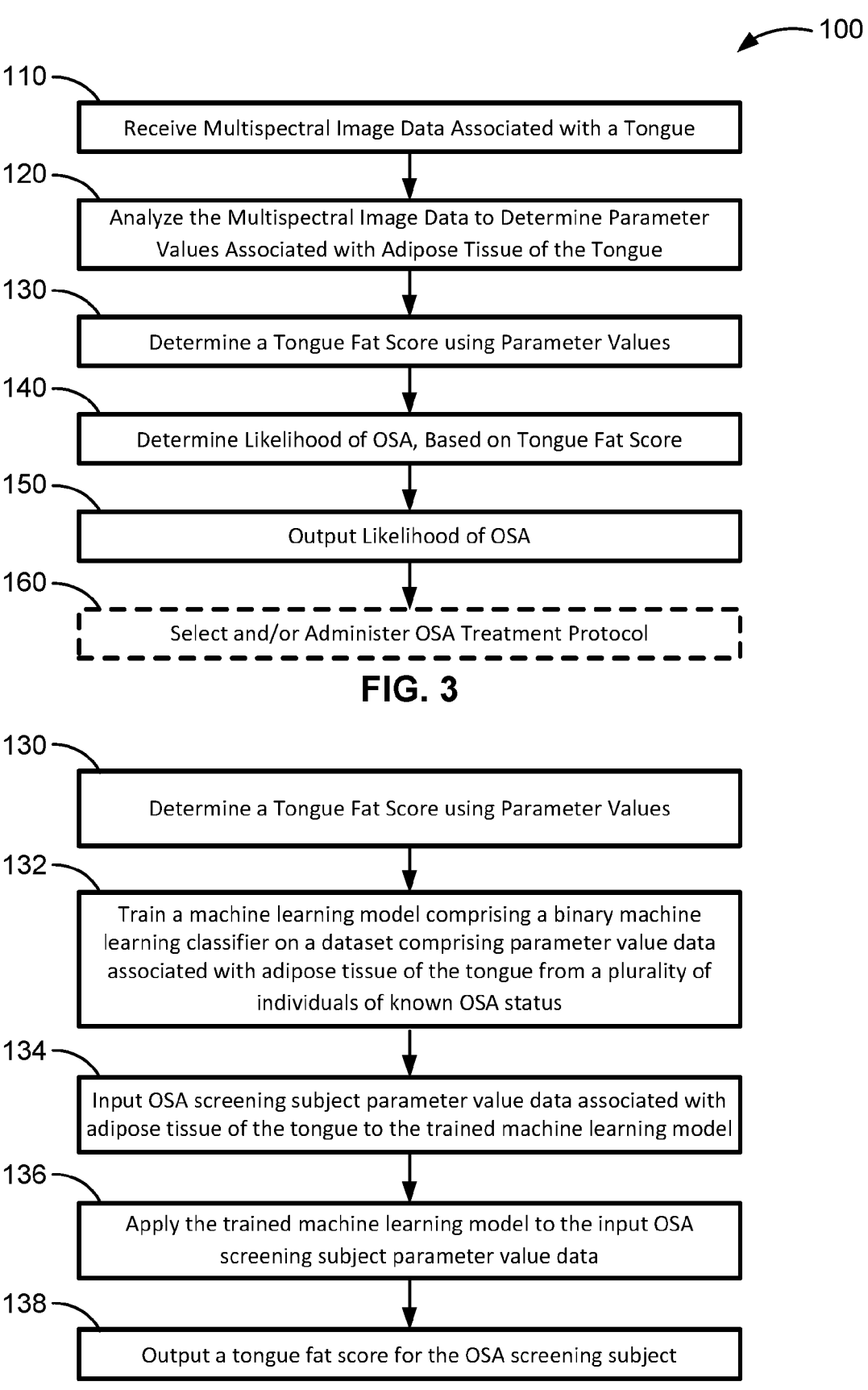

110 — Receive Multispectral Image Data Associated with a Tongue

120 — Analyze the Multispectral Image Data to Determine Parameter Values Associated with Adipose Tissue of the Tongue 130 — Determine a Tongue Fat Score using Parameter Values 140 — Determine Likelihood of OSA, Based on Tongue Fat Score 150 — Output Likelihood of OSA 160 — Select and/or Administer OSA Treatment Protocol

FIG. 3

130 — Determine a Tongue Fat Score using Parameter Values

132 — Train a machine learning model comprising a binary machine learning classifier on a dataset comprising parameter value data associated with adipose tissue of the tongue from a plurality of individuals of known OSA status 134 — Input OSA screening subject parameter value data associated with adipose tissue of the tongue to the trained machine learning model 136 — Apply the trained machine learning model to the input OSA screening subject parameter value data 138 — Output a tongue fat score for the OSA screening subject

FIG. 4

TONGUE FAT SCREENING ASSAY

CROSS REFERENCE TO RELATED APPLICATIONS

This application is a 35 U.S.C. § 371 National Phase Entry of International Patent Application No. PCT/US2022/011581 filed Jan. 7, 2022, which designates the U.S. and claims the benefit of, and priority to, U.S. Provisional Patent Application No. 63/135,881 filed on Jan. 11, 2021, which are hereby incorporated by reference herein in their entirety.

TECHNICAL FIELD

The present disclosure relates generally to methods for detecting and/or predicting the occurrence of sleep apnea.

BACKGROUND

Obstructive sleep apnea (OSA) is a major public health burden affecting greater than 15 million adults in the United States alone and is associated with important medical consequences. The prevalence of OSA is increasing, mirroring the rising weight of the average individual, as obesity is a strong risk factor for the development of OSA.

SUMMARY

According to some implementations of the present disclosure, the likelihood of a subject experiencing sleep apnea (e.g., obstructive sleep apnea) is determined by measuring the degree of tongue fat in a subject using thermal (infrared spectrum) or terahertz (THz gap) imaging techniques. The resulting single or multispectral imaging data can be used to determine one or more parameter values associated with adipose tissue of the tongue including, but not limited to, volume of tongue fat, percent tongue fat, distribution of tongue fat, or area of tongue fat.

According to some implementations of the present disclosure, described herein is a method of predicting a likelihood an individual will experience or is experiencing obstructive sleep apnea, the method comprising: receiving multispectral image data associated with a tongue of the individual; analyzing the imaging data to determine one or more parameter values associated with adipose tissue of the tongue of the individual; determining, based at least in part on the determined one or more parameter values, a tongue fat score; and determining a percentage likelihood that the individual will experience or is experiencing obstructive sleep apnea (OSA) based at least in part on the determined tongue fat score.

According to some implementations of the present disclosure, the imaging data comprises multispectral thermal image data. In another implementation, the imaging data comprises terahertz (THz) radiation image data. In another implementation, the multispectral image data comprises data for a plurality of images. In another implementation, the multispectral image data are collected in the oral cavity of the individual. In another implementation, the parameter values include a location of adipose tissue in the tongue of the individual, a distribution of adipose tissue in the tongue of the individual, an amount of adipose tissue in the tongue of the individual, or any combination thereof. In another implementation, the method further comprises receiving multispectral image data associated with the pharynx of the individual, and analyzing the multispectral image data associated with the pharynx to determine one or more parameter values associated with adipose tissue of the pharynx of the individual. In another implementation, the multispectral image data associated with the pharynx comprises multispectral thermal image data or THz radiation image data. In another implementation, the multispectral image data associated with the pharynx comprises data for a plurality of images. In another implementation, the method further comprises receiving multispectral image or other image data associated with the oral cavity and/or pharynx of the individual, and analyzing those data to determine one or more parameter values associated with the conformation of the oral cavity and/or pharynx of the individual. In another implementation, determining the tongue fat score comprises processing, using a machine learning model comprising a binary machine learning classifier, the received parameter values to output a tongue fat score. In another implementation, the machine learning model was trained on a dataset comprising parameter value data from a plurality of individuals of known OSA status comprising individuals known to experience OSA and individuals known not to experience OSA. In another implementation, determining the tongue fat score comprises comparison of a plurality of parameter values to at least one reference set of parameter values. In another implementation, the reference set of parameter values comprises parameter values from a plurality of individuals of known OSA status comprising individuals known to experience OSA and individuals known not to experience OSA. In another implementation, the method further comprises capturing the multispectral image data associated with the tongue of the individual. In another implementation, the capturing comprises use of a thermal imaging camera or a THz camera. In another implementation, the method further comprises displaying the percentage likelihood on a graphical user interface. In another implementation, the method further comprises determining, based at least in part on the determined percentage likelihood, that the individual is likely to experience OSA, and causing a recommendation to seek treatment for OSA to be communicated to the individual.

According to some implementations of the present disclosure, the method further comprises, before the step of determining a tongue fat score, the step of receiving multispectral image data from a plurality of individuals known to experience or not experience OSA, analyzing the multispectral thermal image data to provide a dataset of parameter values associated with adipose tissue of the tongue of those individuals, and training a machine learning model on the dataset.

According to some implementations of the present disclosure, described herein is a method of determining the amount or distribution of adipose tissue in the tongue of a subject, the method comprising: taking at least one multispectral image of the tongue, thereby providing multispectral image data for the tongue; and processing the at least one multispectral image to identify adipose tissue in the tongue, whereby the amount or distribution of adipose tissue in the tongue is determined.

According to some implementations of the present disclosure, the at least one multispectral image comprises a multispectral thermal image or a THz image. In another implementation, the method further comprises analyzing the multispectral image data to determine one or more parameter values associated with adipose tissue of the tongue of the individual, and determining, based at least in part on the determined one or more parameter values, a tongue fat score that characterizes the amount or distribution of adipose tissue in the tongue.

According to some implementations of the present disclosure, described herein is a system comprising a computer processor and a non-transitory computer-readable storage medium comprising instructions for: receiving multispectral image data associated with a tongue of the individual; analyzing the multispectral image data to determine one or more parameter values associated with adipose tissue of the tongue of the individual; determining, based at least in part on the determined one or more parameter values, a tongue fat score; determining a percentage likelihood that the individual will experience or is experiencing obstructive sleep apnea (OSA) based at least in part on the determined tongue fat score; and outputting the percentage likelihood to a graphical user interface.

BRIEF DESCRIPTION OF THE DRAWINGS

The foregoing and other advantages of the present disclosure will become apparent upon reading the following detailed description and upon reference to the drawings.

FIG. 2B, non-apneic age-matched and ethnicity-matched control). The apneic tongue is much larger and there is increased tongue fat deposition throughout the apneic tongue.

FIG. 3 provides a flowchart of a methodology 100 for the analysis of multispectral image data associated with a tongue according to one implementation of the technology described herein. As shown in the flowchart, multispectral image data are analyzed to permit the determination of a tongue fat score using parameter values and to determine the likelihood of OSA based, at least in part, on the tongue fat score. The tongue fat score is optionally provided as an output, as is the likelihood of OSA, and optionally a selection of a treatment protocol.

FIG. 4 provides a flowchart describing steps 132 to 138 within methodology 100, step 130 applying a machine learning model comprising a binary machine learning classifier to provide a tongue fat score.

Figure 1:
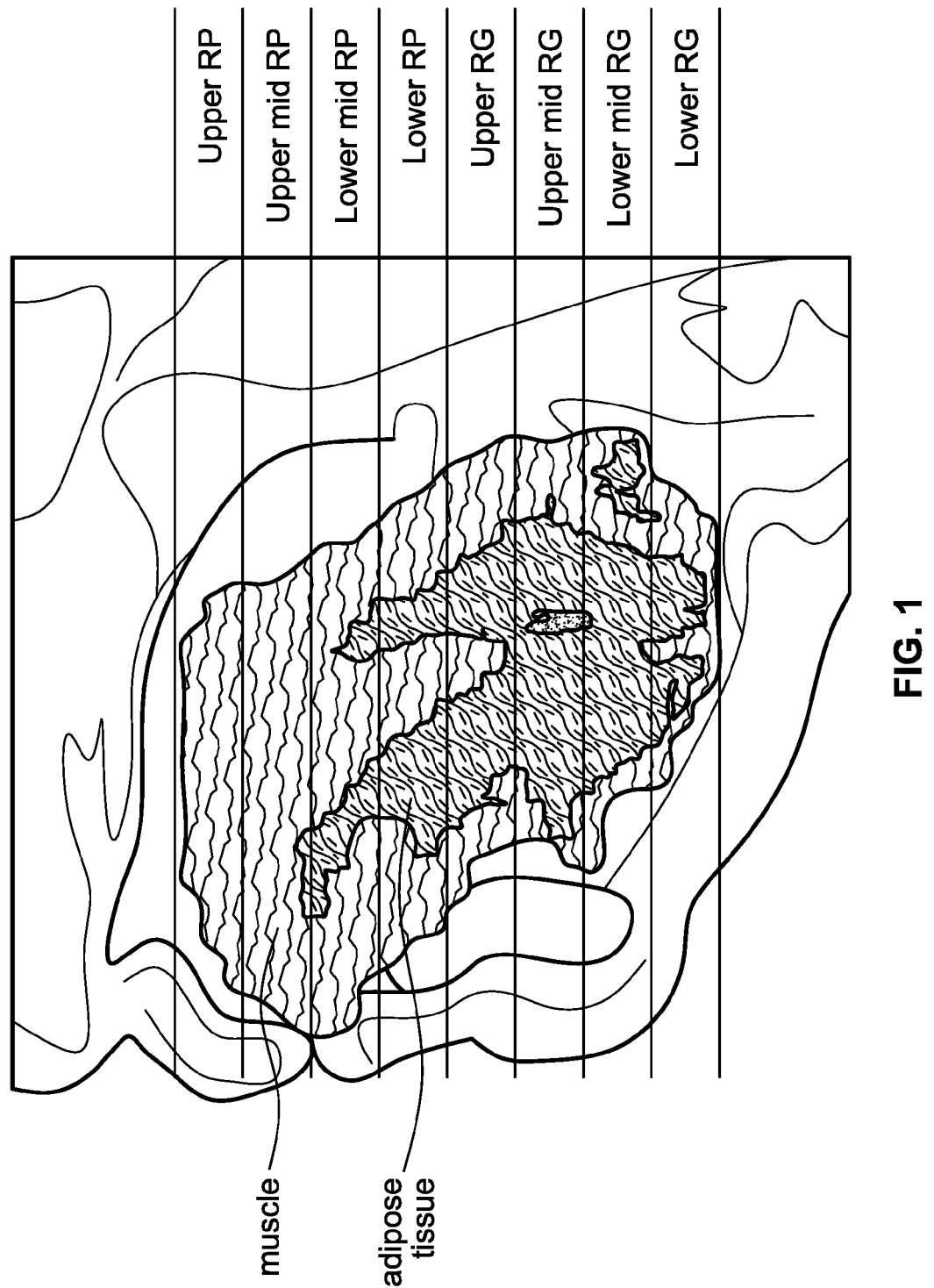
FIG. 1 is a schematic showing a representative three-dimensional volumetric reconstruction of tongue and fat within tongue tissue from a series of 3 mm contiguous axial MR images superimposed on a midsagittal image. Eight sections of a tongue from an apneic individual include data collected from four regions of the retropalatal region (RP) and four regions of retroglossal region (RG). These data indicate that there is substantially more fat at the base of the tongue.
Figure 2B:
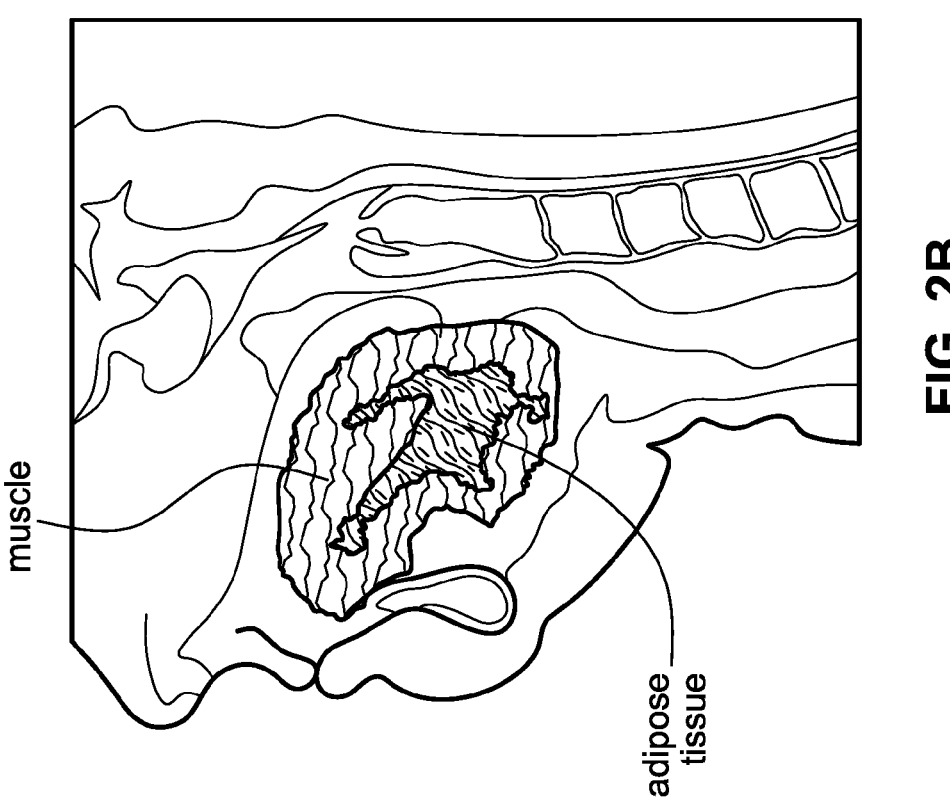
FIG. 2A-2B is a schematic depicting the size and tongue fat content of an apneic subject compared to a control, non-apneic subject. Representative three-dimensional volumetric reconstructions of tongue tissue and fat within the tongue from a 3-mm contiguous axial MRI scan are superimposed on midsagittal images in BMI-matched post-menopausal female patients with OSA (FIG. 2A, subject with OSA.
Figure 2A:
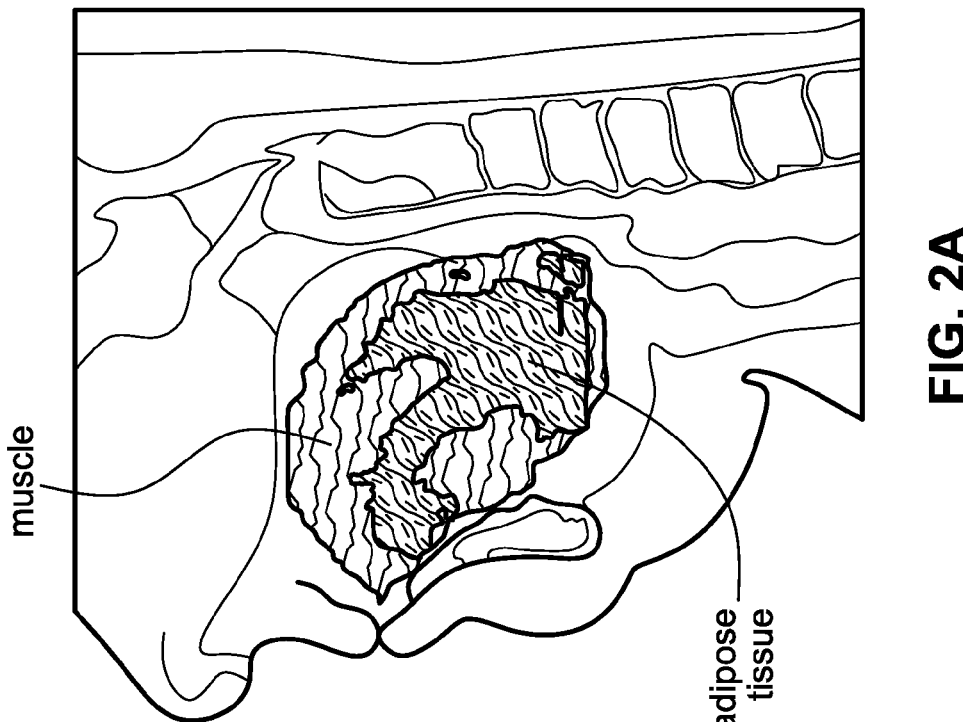

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Provided herein, in part, are methods for predicting the likelihood that a subject will experience obstructive sleep apnea (e.g., moderate to severe OSA based on the Apnea/Hypopnea Index scale) by measuring the amount, distribution and/or other parameters of tongue fat using multispectral thermal imaging. Such methods can also be applied to diagnosing a subject with obstructive sleep apnea. In some implementations, the methods for predicting the likelihood that a subject has OSA do not require a sleep study to monitor or count events of apnea or hypopnea.

Definitions

The terms "patient," "subject" and "individual" are used interchangeably herein, and refer to an animal, particularly a human, that is at risk of or suspected of experiencing obstructive sleep apnea. It is specifically contemplated herein that a subject can be of any developmental age including, but not limited to, a neonate, an infant, a toddler, a child, an adolescent, an adult, post-menopausal, or a geriatric subject. In some implementations, the subject is "obese" as that term is used herein.

As used herein, the term "obesity" or "obese" refers to subjects having a body mass index greater than 30. Body mass index can be calculated by dividing the subject's weight in kilograms by the square of their height in meters.

As used herein, the term "overweight" refers to subjects having a body mass index of at least 25 and less than 30 (i.e., 26, 26.5, 27, 27.5, 28, 28.5, 29, 29.5, 29.9 or any integer therebetween).

As used herein, the term "multispectral data" or "multispectral parameters" refers to the set of images collected under a plurality of distinct optical conditions during a single illumination session. The different optical conditions can include differences in polarization conditions, differences in illumination angle, differences in imaging angle and differences in illumination wavelength.

The terms "increased," or "increase" are each used herein to generally refer to an increase (e.g., tongue fat (volume or percent) or other parameter or value) by a statistically significant amount; for the avoidance of any doubt, the terms "increased," or "increase" means an increase of at least 10% as compared to a reference level or reference subject, for example an increase of at least about 20%, or at least about 30%, or at least about 40%, or at least about 50%, or at least about 60%, or at least about 70%, or at least about 80%, or at least about 90% or up to and including a 100% increase or more, e.g., 2-fold, 3-fold, 4-fold, 5-fold, 10-fold or more, or any increase between 10% and 10-fold or more, as compared to a reference level or reference subject for any given parameter.

As used herein, the term "apneic" refers to a subject having an Apnea/Hypopnea Index (AHI) of at least 5 events per hour, on average. While an AHI of 5 or more does not necessarily warrant aggressive intervention, apneic subjects, including those with an AHI between 5-14 (mild OSA), 15-29 (moderate OSA), and greater than 30 (severe OSA), may benefit from some form of therapy or other intervention. The subject can be obese or non-obese (e.g., overweight, normal weight, or underweight).

As used herein, the term "non-apneic" refers to a subject that has an AHI score of less than 5 events per hour, on average.

Obstructive Sleep Apnea

Sleep Apnea is a sleep disturbance or disorder characterized by abnormal pauses in breathing or instances of abnormally low breathing, during sleep. An "apnea", or basically a pause in breathing can typically last from a few seconds to minutes, and may occur many times over a period of an hour.

In one form of sleep apnea, commonly known as Obstructive Sleep Apnea (OSA), a patient's normal breathing is interrupted by a physical block of the airway. As a result, not enough air reaches a patient's lungs, resulting in decreased airflow to the lungs. Common symptoms of OSA include loud snoring, restless sleep, fatigue and sleepiness during the daytime. In addition to these direct symptoms, the effects of OSA contribute to the development and/or exacerbation of a whole host of other health conditions, including heart disease, stroke, diabetes, memory loss, and other long term health risks.

Positive airway pressure (PAP) is one of the most common treatments for obstructive sleep apnea. PAP treatments (including, continuous positive airway pressure (CPAP), automatic positive airway pressure (APAP), and bi-level positive airway pressure (BPAP) usually involve a patient wearing a mask or a similar device that fits over a patient's nose, or covering both the nose and the mouth of a patient. Usually, a tube connects the mask to a motor that blows air into the mask through the tube. The air pressure can be adjusted based on the needs and comfort level of the patient being treated. Generally, it is the doctor's responsibility to decide what pressure settings are appropriate for the patient.

Other methods of treatment of sleep apnea include nasal valves, surgeries (e.g., to remove and tighten tissue around the airway to the lungs), and dental devices. Such surgeries can involve tongue repositioning, procedures concerning the patient's sinuses and valves, and various palatal techniques.

Obesity is one of the strongest risk factors for the development of OSA as patients with OSA have a higher percentage of adipose deposits in the areas of obstruction, specifically, the soft palate and uvula, base of tongue and lateral pharyngeal walls. The adipose tissue may be up to or greater than 40% of the total volume of tissues in these areas.

The degree of OSA can be assessed clinically using the Apnea-Hypopnea Index (AHI). The AHI is calculated as the average number of apnea/hypopnea events divided by the number of hours of sleep in which the events were counted. The number of events is determined by adding the number of apneas (pauses in breathing) and the number of hypopneas (periods of shallow breathing) that occur each hour. Each apnea/hypopnea event must persist for at least 10 seconds to be counted. Based on this calculation, a subject is diagnosed with a degree of apnea/hypopnea as shown in the Table below:

| Calculated Apnea/Hypopnea Index | Diagnosis |
| --- | --- |
| <5 | Normal (no sleep apnea) |
| 5-15 | Mild sleep apnea |
| 15-30 | Moderate sleep apnea |
| >30 | Severe sleep apnea |

Tongue Fat and Obstructive Sleep Apnea

The tongue is made up of five intrinsic muscles: superior, inferior, longitudinal, transverse, and vertical muscles not attached to any bone, and four extrinsic muscles: genio, hyo, stylo, and palato glossus muscles that are attached to bones. The skeletal muscles in the tongue are arranged in three different planes, which permits the tongue to perform a number of complex movements in every direction. While asleep in the supine position, all of the tongue muscles relax; the muscle mass of the tongue moves back due to weight and gravitational pull resulting in obstruction of the air way causing snoring and obstructive sleep apnea. Increased tongue fat not only increases the size of the tongue, which affects airway size and collapsibility, but can also adversely affect muscle function. It has previously been shown that in apneics, a higher percentage of fat occurs at the base of the tongue, the location where extrinsic muscles anchor the tongue to bone. This increased fat may affect the ability of each of the extrinsic muscles to properly position the tongue away from the airway.

In certain implementations of the present disclosure, the percent volume of tongue fat in the subject is at least 10% higher than the percent volume of fat in a reference or matched non-apneic subject (AHI index<5). The non-apneic subject can be matched for any desired parameter including degree of obesity, sex, ethnicity etc. In other implementations of the present disclosure, the volume of tongue fat in the subject is at least 20% higher, at least 30% higher, at least 40% higher, at least 50% higher, at least 60% higher, at least 70% higher, at least 80% higher, at least 90% higher or 1-fold higher or more than the volume of fat in a matched non-apneic subject. In addition to volume of tongue fat, parameters including the distribution of the adipose tissue, specific locations of the adipose tissue, depth of the adipose tissue, ratio of adipose to lean tissue (or lean to adipose), among others, can contribute to diagnosis or prediction of OSA occurrence.

In certain implementations of the present disclosure, a scan or collection of data regarding tongue fat according to any of the parameters described herein, with accompanying analysis as described herein, can be used to provide a likelihood or status with regard to OSA. In certain implementations of the present disclosure, the process of scanning or collecting such data regarding tongue fat can be used to monitor a subject, e.g., a subject on a weight loss regimen, for changes in tongue fat and accompanying changes in OSA occurrence. In certain implementations of the present disclosure, the collection and analysis of such data can be performed as part of a routine physical examination, as a valuable predictor of OSA and the health problems that often accompany it.

In certain implementations of the present disclosure, the multispectral imaging of the tongue and, optionally the oral cavity and oropharyngeal region can also be used to screen for and/or diagnose cancer. Multispectral imaging, including thermal imaging has been applied to cancer screening, as tumor tissue tends to have a different thermal profile, as well as different water content relative to healthy or non-tumor tissue. As such, in certain implementations of the present disclosure, the multispectral imaging and accompanying analysis of OSA status or risk as described herein can be combined with screening for cancer based on data collected in the same, for example, mouth and throat imaging scan or scan session.

In certain implementations of the present disclosure, the methods described herein apply multispectral imaging encompassing any imaging approach that can discern adipose from muscle tissue in the tongue, optionally in conjunction with similar measurements in the oropharyngeal region, to the diagnosis or prediction of OSA occurrence or risk. Thus, while multispectral thermal imaging, or terahertz imaging are examples of imaging modalities described herein for this purpose, other optical or electromagnetic imaging approaches, optionally in combination with machine learning as also described herein, can also be applied to the diagnosis or prediction of OSA occurrence or risk in an analogous manner.

Multi-Spectral Imaging

Multi-spectral imaging, including multispectral thermal imaging, refers to the simultaneous acquisition of imaging data from both the thermal, infra-red spectrum and the visible spectrum, which can be combined for analysis of e.g., tongue fat. Multiple images of the tongue can be simultaneously captured from the same point of view, where each image corresponds to a different portion of the electromagnetic spectrum. By way of example and not limitation, consider two images, one corresponding to the visible spectrum and one from the thermal infrared spectrum. In one implementation, the components necessary to image both the thermal and visible spectrum are provided in a single unit or housing. In alternate implementations of the present disclosure, a first imaging device can image the visible spectrum, while the thermal spectrum is captured using a second imaging device.

The thermal and visible (and optionally UV) wavelengths can be separated by filters or detected via the use of instruments that are sensitive to particular wavelengths. Spectral imaging can allow extraction of additional information the human eye fails to capture with its visible receptors for red, green and blue. The multispectral thermal imager used herein can comprise filters to permit imaging of wavelengths from at least the thermal infrared range (~10400-12500 nm) and the visible range (~380 to 700 nm). Exemplary filters for wavelengths in other ranges can be used with the methods described herein including filter for blue (~450-520 nm), green (~520-600 nm), red (600-690 nm), near infrared (NIR; 750-950 nm), mid-infrared (MIR; 1550-1750 nm), far-infrared (FIR; 2080-2350 nm) and other or thermal infrared (10400-12500 nm).

As will be recognized by those of skill in the art, for different parts of a human body, the heat resistance rate (thermal conductivity) is different. For example, for fatty tissue (adipose), the heat resistance rate R is about 0.1 to 0.15° C./cm and for muscle R is about 0.2° C./cm. Thus, the thermal images obtained as described herein can differentiate adipose tissue from neighboring muscle tissue by the amount of heat produced and imaged. Adipose tissue also has less water (about 10%) than muscle tissue (about 75%), and interactions between optical energy and water vs. fat are significantly different, such that measurements of reflectance and/or absorption at particular wavelengths can provide sensitive determination of the amount of fat vs lean tissue in a given location. Fat has an absorbance peak in the NIR spectrum at 928 nm. NIR cameras have been used to measure body fat—see, e.g., Rosenthal, R. D., The Use of Near-IR Light to Measure Body Fat, January 1991, available on the world wide web at futrex.com/wp-content/uploads/2015/03/The-Use-of-Near-IR-to-Measure-Body-Fat.pdf, and references therein. See also Mustafa, F. H. et al., Biomed. Eng. Online 16: 14 (2017), "Near infrared spectroscopy for body fat sensing in neonates: quantitative analysis by GAMOS simulations," which describes the use of NIR spectroscopy for non-invasive body fat measurements, and Salamunes et al., "Application of thermal imaging for the assessment of body composition in humans," in "Thermal Imaging: types, advancements and applications (pp 61-79), Edition 1, Chapter 3 (Nova Science Publishers, C. Strickland, ed.).

Multispectral Imaging Devices

There are a range of multispectral imaging devices known and available in the art. According to some implementations of the present disclosure, a multispectral imaging device can obtain thermal image data for a tongue or for associated oral or oropharyngeal tissues or structures. Such a device can optionally also obtain image data in the visible or other ranges of the electromagnetic spectrum; overlay of, for example visible and thermal image data can provide or augment information regarding the location and distribution of adipose tissue in the tongue, among other parameters.

According to some implementations of the present disclosure, a multispectral imaging device can obtain thermal or other image data for tissues and structures within the oral or oropharyngeal cavity. Such devices can include, for example, a device that obtains thermal or other image data from outside the oral or oropharyngeal cavity, e.g., by imaging a subject's face or head, whether in profile or from a frontal location or both. Alternatively, devices that obtain thermal, and optionally visible or other spectrum image data through a scope that is inserted into the oral or oropharyngeal cavity can also be used; such devices include, but are not limited to a thermal camera, for example an IR camera, located at a distal end of an endoscope so as to be facing tissue or structure(s) to be imaged. Such a device can facilitate, for example, obtaining detailed or high resolution multispectral image data for the base of the tongue or for other desired structures in the oropharyngeal region.

According to some implementations of the present disclosure, a device for multispectral imaging of a tongue or associated tissues or regions can cycle through imaging a range, such as a continuous range, of the electromagnetic spectrum, so as to collect multispectral image data. In other implementations of the present disclosure, a device can collect image data for selected portions of the spectrum, e.g., a range of the visible spectrum and a range of the infrared spectrum.

According to some implementations of the present disclosure, the device for obtaining multispectral image data can obtain a single image or a plurality of such images, e.g., as "snapshots." Such images can be taken from a plurality of different angles or positions if so desired. In other implementations, the image data are video image data, obtained, for example, by scanning an imaging device over an area to be imaged. Images of the same field of view as a visible system but recording video of the temperature distribution can be obtained. The acquired raw data can be post processed and output in 1D, 2D or 3D, depending upon software used for processing.

According to some implementations of the present disclosure, the device for obtaining multispectral image data can be a Forward Looking Infrared or "FLIR" camera. Such devices, including devices with high resolution are not only available, but increasingly available in smaller and less expensive configurations than before. As but one example, the FLIR ONE Pro LT iOS device attaches to a smartphone and provides multispectral thermal imaging that can be adapted for use in the methods described herein.

According to some implementations of the present disclosure, the device for obtaining multispectral image data can be a terahertz (THz) imager. The terahertz spectrum generally refers to the portion of the electromagnetic spectrum between 100 GHz and 10 Thz, or wavelengths of 3 mm to about 30 μm. The relatively long THz wavelengths can penetrate much further into biological tissue than visible or near infrared light, but they do not pose the risks of damage to tissues posed by UV or X-ray irradiation. Because THz radiation excites rotational and vibrational modes of some biological molecules, THz radiation provides effective tissue-differentiating properties (see, e.g., Mittleman et al., IEEE J. Selected Top. Quantum Electronics 2: 679-692 (1996), Humphreys et al., Conference Proceedings, IEEE Engineering in Medicine and Biology Society Conference 2: 1302-1305 (2004), and U.S. Pat. No. 9,269,731, each of which is incorporated herein by reference). Imaging in the THz range generally takes advantage of differences in optical reflection due to water content. See, e.g., Wilmink et al., J. Biomed. Optics 16: 047006 (2011), "Development of a compact terahertz time-domain spectrometer for the measurement of the optical properties of biological tissues," which describes the use of a compact THz spectroscopy imaging device as applied to discerning muscle, adipose and skin tissues.

Reference Samples

The results obtained from multispectral thermal images (e.g., volume of tongue fat; percentage of tongue fat, distribution of tongue fat, etc.) in a subject can be compared to a multispectral thermal reference value, or data from multispectral thermal images from a reference population or reference subject. As used herein, the term "reference value" or "reference set of parameter values" refers to a reference value, set of values, or range of values, obtained from a subject having obstructive sleep apnea or a population thereof. Alternatively, the reference value can be obtained from a non-apneic subject or population thereof. In some implementations of the present disclosure, the reference value is obtained from the same subject as a baseline prior to weight loss or gain. The reference sample can be stored as a value(s) on a computer or PDA device to permit comparison with a value obtained from a subject using the methods described herein. One of skill in the art can determine an appropriate reference sample for use with the methods described herein.

Generally, when non-apneic subject(s) are used as a reference value or reference population, a greater amount, or an increase in the amount of tongue fat measured using multispectral thermal imaging over a reference value indicates that the subject is at an increased risk of obstructive sleep apnea as compared to a non-apneic subject. It is specifically contemplated herein that volume or percent tongue fat in a subject can be used to diagnose the degree of obstructive sleep apnea (e.g., on the AHI scale). For example, the larger degree of increase in tongue fat in a subject over a reference can be predictive of a more severe degree of OSA.

Reference information can include a reference dataset comprising multispectral image data from a cohort of subjects having known OSA status, e.g., known AHI values obtained through sleep study or other means. Such reference information can include, in addition to multispectral thermal image data and AHI values, information regarding tongue fat amount, distribution or locations, proportion and/or ratio, among other tongue fat-related parameters, as well as information regarding the subjects' BMI, age, sex, tongue shape or dimensions, oropharyngeal shape or dimensions, general health status or presence of additional conditions (e.g., diabetes, cardiovascular disease, etc.) or other parameters. Determination of Tongue Fat Score and/or Likelihood or Diagnosis of OSA According to some implementations of the present disclosure, tongue fat score is determined by analysis of multispectral image data from the tongue to determine one or more of the amount, relative proportion, ratio, distribution and location(s) of adipose tissue in the tongue. In some implementations of the present disclosure, the analysis includes such values for the tongue as a whole, while in others, the analysis can consider values relating to particular locations or sectors of the tongue. As a non-limiting example, the amount and/or proportion of adipose tissue at the base of the tongue can provide information relevant to a likelihood of experiencing OSA.

According to some implementations of the present disclosure, the determination of tongue fat score involves a comparison of one or more parameter values relating to the amount, relative proportion, ratio, distribution and location(s) of adipose tissue in the tongue with one or more reference values for such parameter(s). The reference values can be obtained from one or more, optionally a plurality, e.g., 2, 3, 4, 5 or more, e.g., 10 or more, 50 or more, 100 or more, 500 or more, 1000 or more reference samples of known OSA status. In some implementations of the present disclosure, such reference values can be classified according to their relative impact on likelihood of OSA, such that a cumulative value for the various parameters correlates with likelihood of experiencing OSA.

According to some implementations of the present disclosure, tongue fat score considered alone can be highly predictive of likelihood of experiencing OSA. In such implementations of the present disclosure, a tongue fat score that meets or exceeds a given threshold can alone provide a strong indication that the subject will experience OSA. In other implementations of the present disclosure, tongue fat score can be considered in addition to or in combination with other parameters that can potentially influence the subject's likelihood of experiencing OSA. Non-limiting examples include the subject's age, sex, weight, BMI, oropharyngeal dimensions, neck diameter (or circumference), facial dimensions or facial scan data, general health status or presence of additional conditions (e.g., diabetes, cardiovascular disease, etc.) or other parameters, e.g., other parameters associated with susceptibility to OSA.

According to some implementations of the present disclosure, the methods disclosed herein apply a machine learning model for processing multispectral image data to generate a tongue fat score and/or to provide a prediction of likelihood or a diagnosis regarding OSA. In one implementation, the machine learning model comprises a binary machine learning classifier, applied to parameter values regarding adipose tissue of the tongue obtained by analysis of the multispectral image data, to determine a tongue fat score. In another implementation, the machine learning classifier is trained on a training or reference dataset comprising, for example, multispectral thermal image data and/or values or representations for the amount, location and/or distribution of tongue fat, ratio of lean to adipose tissue (or adipose to lean tissue) in the tongue, AHI, optionally including further values or representations for the subjects' age, sex, weight, BMI, oropharyngeal dimensions, neck diameter (or circumference), facial dimensions or facial scan data, general health status or presence of additional conditions (e.g., diabetes, cardiovascular disease, etc.) or other parameters, e.g., other parameters associated with susceptibility to OSA. The machine learning classifier trained on such a reference dataset provides an algorithm applicable to a dataset comprising multispectral image data and/or parameter values determined therefrom regarding adipose tissue of the tongue of a subject being screened or evaluated for likelihood of experiencing OSA. Thus, while in some implementations parameters concerning adipose tissue of the tongue can alone provide diagnostic or predictive information regarding occurrence, likelihood or risk of OSA, in other implementations the data related to adipose tissue of the tongue, or a risk score derived from or based upon it, can be combined with data relating to other parameters or conditions that influence the occurrence, likelihood or risk of OSA or other health conditions to train a machine learning classifier with a potential improvement in predictive or diagnostic accuracy.

According to some implementations of the present disclosure, the binary machine learning classifier includes at least one of: a random forests classifier, a logistic regression classifier, a decision tree classifier, a Bayesian network classifier, a classification and regression tree, and a neural network classifier.

According to some implementations of the present disclosure, determining a likelihood (e.g., a percentage likelihood) that the individual will experience or is experiencing obstructive sleep apnea (OSA) includes detecting a tongue fat score value that crosses one or more predetermined OSA likelihood or status thresholds. It should be understood that the absolute value of a tongue fat score will depend upon how the tongue fat score is represented. As non-limiting examples, a tongue fat score can be scaled from 0 to 1.0, with 0 correlating to the lowest proportions or values of tongue fat parameters and 1.0 the highest, or from 0 to 100, 0 correlating to the lowest proportions or values of tongue fat parameters and 100 the highest. Other representations and scales can also be used without changing the principles underlying the methods described herein. As a non-limiting example, in one implementation, a tongue fat value that exceeds an OSA likelihood or status threshold by as little as 1% can indicate an increased likelihood of experiencing OSA sufficient to warrant a recommendation of therapy for OSA. As another non-limiting example, a tongue fat value that exceeds an OSA likelihood or status threshold by 1% to, e.g., 20%, can indicate an increased likelihood of experiencing OSA sufficient to warrant a recommendation for a sleep study or other diagnostic measure, without yet warranting a recommendation for therapy for OSA. In that example, a tongue-fat value that exceeds an OSA likelihood or status threshold by greater than 20% could warrant a recommendation of therapy for OSA. As will be understood by one of ordinary skill in the art, the difference in these examples depends upon how tongue fat scores and/or OSA likelihood as related thereto are represented, rather than differences in the principles underlying the technology.

According to some implementations of the present disclosure, tongue fat score and/or OSA likelihood thresholds can be determined, for example, by the machine learning classifier as applied to the reference or training dataset for which OSA occurrence and/or severity is known.

According to some implementations of the present disclosure, a method of treating OSA in a subject includes receiving output from a machine learning model indicative of the subject having or being at increased likelihood of having OSA, and recommending and/or administering a treatment for the OSA to the subject. The output is generated by: receiving multispectral image data associated with a tongue of the individual; analyzing the multispectral image data to determine one or more parameter values associated with adipose tissue of the tongue of the individual; determining, based at least in part on the determined one or more parameter values, a tongue fat score; and determining that the individual will experience or is experiencing obstructive sleep apnea (OSA) based at least in part on the determined tongue fat score. In some examples, determining that the tongue fat score provides an indication that the subject has or is likely to experience OSA includes detecting a tongue fat score that crosses one or more predetermined OSA status or indicator thresholds.

According to some implementations of the present disclosure, the screening of a subject for likelihood of experiencing OSA as described herein can be performed once, or, for example, on a repeat basis, including but not limited to screening on a regular basis, e.g., monthly, annually (e.g., as part of an annual physical), or on any schedule recommended or established by a clinician, including not limited to a sleep specialist.

EXAMPLES

Example 1: Multispectral Thermal Imaging of Tongue Fat

Multispectral thermal imaging is used to measure the amount of tongue fat in (i) obese subjects having severe apnea (>30 on the AHI scale), (ii) obese subjects without sleep apnea (<5 on the AHI scale), non-obese subjects having no sleep apnea (<5 on the AHI scale) and non-obese subjects having at least a moderate degree of sleep apnea or severe sleep apnea (>15 or >30 on the AHI scale). In one aspect, the top of the tongue is scanned from the base of the tongue towards the tip with a multispectral thermal imaging device(s). The bottom of the tongue can also be scanned from the attachment to the tip of the tongue. The scan will start as far back on the tongue as is tolerated by the subject. In another aspect, the entirety of the top of the tongue and/or the bottom of the tongue are imaged simultaneously (e.g., a "snapshot"). In such aspects, the subject can be instructed to stick their tongue out as far as possible and to hold still to provide clear images. In other aspects, the adipose tissue and tongue size can be assessed using in real-time using a scan. Measurements of the size or total area of the tongue are also performed.

From these measurements, the volume of fat in the tongue can be determined as percent fat over the total area of the tongue. In addition, the distribution of fat, which is generally higher at the base of the tongue, can also be assessed. These measurements can be manually calculated directly from the images received from the multispectral thermal imaging camera by stacking images obtained from different depths (or from the top and bottom scans) to form a 3-dimensional view of the tongue and selecting for areas of fat via image analysis. Optionally, data from the images is used to train a machine learning algorithm, or, optionally, fed into an algorithm trained on similar data from a reference dataset. This approach can provide output based upon not just the overall percentage of tongue fat, but the volume of that fat, and the distribution of that fat in two or three dimensions as an indicator of likelihood of experiencing OSA and the severity of such OSA, e.g., on the AHI scale.

Example 2: Tongue Fat Analysis Via Multispectral Imaging Applied to Prediction, and Optionally, Treatment of OSA Referring generally to FIG. 3, methodology 100 provides an exemplary method of predicting OSA based on tongue fat, according to some implementations of the present disclosure. The exemplary methodology 100 begins at step 110 with receiving multispectral image data associated with a tongue. In some examples, the multispectral image data received at step 110 includes multispectral image data obtained for a tongue of a subject, e.g., a subject being screened for likelihood of experiencing OSA. In some examples, the multispectral image data received can be stored clinical data, experimental data, or test data. Therefore, step 110 provides for receiving real-time measurements from a patient but can also include receiving stored data.

According to some implementations of the methodology 100, and more specifically at step 110, the multispectral image data can comprise thermal image data, e.g., image data obtained using a thermographic camera. Such cameras generally detect radiation in the long infrared wavelengths, on the order of about 9,000 to 14,000 nanometers. The data are generally processed to provide a thermal image, or thermogram, which can be static, like a "snap shot," or dynamic, e.g., as a video image. The camera can optionally obtain data in the visible range, or a second, visible range camera can be used to image the same tongue, preferably from the same angle(s), and the visible range data can optionally be overlaid with the thermal range data to provide a combined image highlighting thermal characteristics of the imaged tongue. In other implementations, at step 110, the multispectral image data received can include image data obtained with a terhertz (THz) camera, detecting reflection or absorption of electromagnetic radiation generally in the range of 300 GHz to 30 THz. The data obtained with a THz camera can, like the thermal image data, include static or dynamic image data, and can optionally be combined with visible image data obtained for the same tongue (and preferably from the same angle(s)) to provide a combined image highlighting THz reflection and/or absorption characteristics of the imaged tongue.

At step 120, the methodology 100 provides for analyzing the multispectral image data received to determine parameter values associated with adipose tissue of the tongue. Adipose or fat tissue has different thermal properties than non-adipose tissue such as muscle or bone, which provides for distinguishing adipose from non-adipose tissue. Adipose-related parameters that can be determined by analysis of multispectral image data, including thermal image data, can include, as non-limiting examples: the volume of fat or adipose tissue in the tongue, including total volume and localized volume(s); the mass of fat or adipose tissue in the tongue, including total mass and localized mass; the distribution of fat or adipose tissue in the tongue, including, but not limited to the occurrence or density of fat or adipose tissue over the whole of the tongue, and/or the occurrence or density of fat or adipose tissue in sectors or regions of the tongue (e.g., the base of the tongue, one or more quadrants representing, for example, the front or tip of the tongue, one or more sides of the tongue, a central region of the tongue, etc.), the depth of a fat or adipose tissue deposit or deposits in the tongue as a whole or in one or more sectors or regions of the tongue; and the ratio of lean or non-adipose tissue to fat or adipose tissue in the tongue as a whole or in one or more sectors or regions of the tongue. The analysis can generally comprise processing the data using software to provide a representation, including but not necessarily limited to an image on a screen, of the tongue adipose tissue parameters. Where the representation of the data includes an image on a screen, the parameter values can be represented, for example, by visible spectrum color(s) assigned to the values for the parameters—as a non-limiting example, the density of fat can be assigned colors on the visible spectrum, with, e.g., the red end of the spectrum corresponding to higher value adipose-associated parameter values and the violet end of the spectrum corresponding to lower parameter values.

At step 130, the methodology 100 provides for the determination of a tongue fat score using or based at least in part on the parameter values determined in step 120. Whether the adipose-associated parameter values are represented visually, e.g., as an image on a screen, or as values in one or more datasets, the tongue fat score can be determined, for example, based on the specific values for each parameter determined. In some implementations of the present disclosure, each parameter is assessed for whether it is less than, meets or exceeds a threshold value for that parameter, or for where it falls on a range of values for that parameter. Such assessment or grading can transform the specific parameter values to a relative or comparative value, based for example, on measurements of that parameter for a population of individuals, e.g., a population with known incidence of OSA. In some implementations of the present disclosure, the relative or comparative values for a plurality of different parameters, up to and including all such different parameters determined, can then be assessed to arrive at a tongue fat score.

At step 140, the methodology 100 provides for the determination of a likelihood that the subject experiences or will experience OSA. The likelihood can be expressed as a percentage, or on any other graded scale that correlates tongue fat score, optionally in combination with consideration of other factors including, but not limited to age, sex, weight, height, BMI, oropharyngeal dimensions, and status for other risk factors, such as diabetes. In some implementations of the present disclosure, determination of the likelihood of experiencing OSA at step 140 can comprise comparison of the tongue fat score for a subject being screened with the tongue fat scores of a plurality of individuals for whom the occurrence and severity of OSA, also referred to herein as an "OSA status," is known. In some implementations of the present disclosure, the tongue fat scores for a plurality of individuals for whom OSA status is known provides a scale that correlates tongue fat score with OSA status, such that the tongue fat score of a subject being screened for OSA permits a determination of the likelihood of the subject experiencing OSA.

With reference to FIG. 4, according to some implementations of the methodology 100, the step 130 determination of a tongue fat score comprises use of a machine learning model comprising a binary machine learning classifier to process the received parameter values to provide or output a tongue fat score. In various implementations, the binary machine learning classifier can include, for example, a random forests classifier, a logistic regression classifier, a decision tree classifier, a Bayesian network classifier, a classification and regression tree, a neural network classifier, or the like, or in any combination thereof.

According to some implementations, step 130, determining a tongue fat score using parameter values, comprises the steps: 132, training a machine learning model comprising a binary machine learning classifier on a dataset comprising parameter value data associated with adipose tissue of the tongue from a plurality of individuals of known OSA status; 134, inputting or sending parameter value data associated with adipose tissue of the tongue from a subject being screened for OSA to the machine learning model trained in step 132; 136, applying the trained machine learning model to the parameter value data from the subject being screened to generate a tongue fat score for the subject; and 138, outputting the tongue fat score for the screening subject. The output can be, for example, to a display or other user-accessible device, to a memory, e.g., for access by one or more additional algorithms, or directly to one or more additional algorithms. Such one or more additional algorithms can include, for example, a further machine learning model comprising a binary machine learning classifier that processes a tongue fat score in combination with one or more further parameters associated with OSA to determine a likelihood of OSA.

One or more elements or aspects or steps, or any portion(s) thereof, from one or more of any of the above implementations and/or the below claims can be combined with one or more elements or aspects or steps, or any portion(s) thereof, from one or more of any of the other above implementations and/or below claims or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

The invention claimed is:

1. A method of predicting a likelihood an individual will experience or is experiencing obstructive sleep apnea, the method comprising:

receiving multispectral image data associated with a tongue of the individual, wherein the multispectral image data comprises terahertz (THz) radiation image data;

analyzing the multispectral image data to discern adipose tissue of the tongue of the individual from muscle, and to determine one or more parameter values associated with adipose tissue of the tongue of the individual selected from a location of adipose tissue in the tongue of the individual, a distribution of adipose tissue in the tongue of the individual, an amount of adipose tissue in the tongue of the individual or a combination thereof;

determining, based at least in part on the determined one or more parameter values, a tongue fat score; and determining a percentage likelihood that the individual will experience or is experiencing obstructive sleep apnea (OSA) based at least in part on the determined tongue fat score.

2. The method of claim 1, wherein the multispectral image data further comprises thermal image data.

3. The method of claim 1, wherein the multispectral image data comprises data for a plurality of images.

4. The method of claim 1, further comprising receiving multispectral image or other image data associated with the oral cavity and/or pharynx of the individual, and analyzing those data to determine one or more parameter values associated with the conformation of the oral cavity and/or pharynx of the individual.

5. The method of claim 1, wherein the determining the tongue fat score comprises processing, using a machine learning model comprising a binary machine learning classifier, the received parameter values to output a tongue fat score.

6. The method of claim 1, wherein the determining the tongue fat score comprises comparison of a plurality of parameter values to at least one reference set of parameter values.

7. The method of claim 6, wherein the reference set of parameter values comprises parameter values from a plurality of individuals of known OSA status comprising individuals known to experience OSA and individuals known not to experience OSA.

8. The method of claim 1, further comprising capturing the multispectral image data associated with the tongue of the individual.

9. The method of claim 8, wherein the capturing comprises use of a thermal imaging camera or a THz camera.

10. The method of claim 1, further comprising displaying the percentage likelihood on a graphical user interface.

11. The method of claim 1, further comprising determining, based at least in part on the determined percentage likelihood, that the individual is likely to experience OSA, and causing a recommendation to seek treatment for OSA to be communicated to the individual.

12. The method of claim 1, further comprising, before the step of determining a tongue fat score, the step of receiving multispectral image data from a plurality of individuals known to experience or not experience OSA, analyzing the multispectral thermal image data to provide a dataset of parameter values associated with adipose tissue of the tongue of those individuals, and training a machine learning model on the dataset.

13. A system comprising:

a control system comprising one or more processors; and a memory having stored thereon machine readable instructions;

wherein the control system is coupled to the memory, and the method of claim 1 is implemented when the machine executable instructions in the memory are executed by at least one of the one or more processors of the control system.

14. A system for communicating one or more indications to a user, the system comprising a control system configured to implement the method of claim 1.

15. The method of claim 1, wherein the method for predicting the likelihood that the individual will experience or is experiencing obstructive sleep apnea (OSA) does not require a sleep study to monitor or count events of apnea or hypopnea.

16. A method of determining the amount or distribution of adipose tissue in the tongue of a subject, the method comprising:

taking at least one multispectral image of the tongue, wherein the at least one multispectral image comprises a THz radiation image, thereby providing multispectral image data for the tongue; and processing the at least one multispectral image to identify adipose tissue in the tongue and discern adipose tissue of the tongue from muscle, whereby the location, amount or distribution of adipose tissue in the tongue is determined.

17. The method of claim 16, wherein the at least one multispectral image further comprises a thermal image.

18. The method of claim 16, further comprising analyzing the multispectral image data to determine one or more parameter values associated with adipose tissue of the tongue of the individual, and determining, based at least in part on the determined one or more parameter values, a tongue fat score that characterizes the amount or distribution of adipose tissue in the tongue.

19. A system comprising a computer processor and a non-transitory computer-readable storage medium comprising instructions for:

receiving multispectral image data associated with a tongue of the individual, wherein the multispectral image data comprises THz radiation image data;

analyzing the multispectral image data to discern adipose tissue of the tongue of the individual from muscle, and to determine one or more parameter values associated with adipose tissue of the tongue of the individual selected from a location of adipose tissue in the tongue of the individual, a distribution of adipose tissue in the tongue of the individual, an amount of adipose tissue in the tongue of the individual or a combination thereof;

determining, based at least in part on the determined one or more parameter values, a tongue fat score;

determining a percentage likelihood that the individual will experience or is experiencing obstructive sleep apnea (OSA) based at least in part on the determined tongue fat score; and outputting the percentage likelihood to a graphical user interface.

* * * * *